United States Patent
Levecq et al.

(10) Patent No.: US 10,031,326 B2
(45) Date of Patent: Jul. 24, 2018

(54) SYSTEM AND METHOD OF EDGE-ILLUMINATION MICROSCOPY

(71) Applicants: IMAGINE OPTIC, Orsay (FR); CENTRE NATIONAL DE LA RECHERCHE SCIENTIFIQUE—CNRS, Paris (FR); UNIVERSITÉ DE BORDEAUX SEGALEN, Bordeaux (FR)

(72) Inventors: Xavier Levecq, Gif-sur-Yvette (FR); Virgile Viasnoff, Vanves (FR); Jean-Baptiste Sibarita, Talence (FR); Vincent Studer, Bordeaux (FR); Rémi Galland, Pessac (FR)

(73) Assignees: IMAGINE OPTIC, Orsay (FR); CENTRE NATIONAL DE LA RECHERCHE SCIENTIFIQUE (CNRS), Paris (FR); Université de Bordeaux, Bordeaux (FR)

( * ) Notice: Subject to any disclaimer, the term of this patent is extended or adjusted under 35 U.S.C. 154(b) by 0 days.

(21) Appl. No.: 14/914,844

(22) PCT Filed: Aug. 27, 2014

(86) PCT No.: PCT/EP2014/068139
§ 371 (c)(1),
(2) Date: Feb. 26, 2016

(87) PCT Pub. No.: WO2015/028493
PCT Pub. Date: Mar. 5, 2015

(65) Prior Publication Data
US 2016/0202462 A1    Jul. 14, 2016

(30) Foreign Application Priority Data

Aug. 28, 2013  (FR) ...................... 13 58226

(51) Int. Cl.
*G01N 21/64*  (2006.01)
*G02B 21/06*  (2006.01)
(Continued)

(52) U.S. Cl.
CPC ......... *G02B 21/06* (2013.01); *G01N 21/6428* (2013.01); *G01N 21/6458* (2013.01);
(Continued)

(58) Field of Classification Search
CPC .... G02B 21/0032; G02B 21/16; G02B 21/26; G01N 21/6458; G01N 221/06113; G01N 2201/02
See application file for complete search history.

(56) References Cited

U.S. PATENT DOCUMENTS 5,710,631 A * 1/1998 Bou-Ghannam ...... G01N 21/88
356/495
6,208,886 B1 * 3/2001 Alfano ................. A61B 5/0073
250/341.1
(Continued)

FOREIGN PATENT DOCUMENTS

FR       2971693 A1    8/2012
WO    2014/009080 A1   1/2014

OTHER PUBLICATIONS

R. Jorand et al.; "Deep and Clear Optical Imaging of Thick Inhomogeneous Samples"; PLoS ONE, vol. 7, Issue 4, e35795, doi:10.1371/journal.pone.0035795, Apr. 25, 2012 (9 pages).
(Continued)

*Primary Examiner* — Kiho Kim
(74) *Attorney, Agent, or Firm* — Osha Liang LLP

(57) ABSTRACT

According to one aspect, the invention concerns a method for microscopy of a thick sample arranged on a sample support, with edge-illumination of the sample. The method comprises, in particular, emitting at least one illumination
(Continued)

beam (1), forming, from the illumination beam, an illumination surface, focusing the illumination surface in the sample by means of a microscope lens (120) and deflecting the illumination surface originating from the microscope lens, in order to form a transverse illumination surface, located in a plane substantially perpendicular to the optical axis of the microscope lens. The method further comprises forming, by means of said microscope lens (120), the image of an area of the sample illuminated by the transverse illumination surface on a detection surface (131) of a detection device (130), scanning the illumination beam, allowing the transverse illumination surface to move along the optical axis of the microscope lens, and superimposing the object imaging surface and the transverse illumination surface, by focusing means comprising means separate from the means for the relative axial movement of the microscope lens and the sample.

11 Claims, 4 Drawing Sheets

(51) Int. Cl.
  *G02B 21/16* (2006.01)
  *G02B 21/24* (2006.01)
  *G02B 21/36* (2006.01)
  *G02B 27/00* (2006.01)
(52) U.S. Cl.
  CPC ............ *G02B 21/16* (2013.01); *G02B 21/241* (2013.01); *G02B 21/361* (2013.01); *G02B 27/0068* (2013.01); *G01N 2201/0638* (2013.01); *G01N 2201/06113* (2013.01); *G01N 2201/10* (2013.01)

(56) References Cited

U.S. PATENT DOCUMENTS

| | | |
|---|---|---|
| 7,974,003 B2 | 7/2011 | Seale et al. |
| 2006/0012855 A1 | 1/2006 | Wolleschensky |
| 2007/0047070 A1* | 3/2007 | Sander .................. G02B 21/18 359/368 |
| 2009/0316141 A1* | 12/2009 | Feldkhun ........... G01N 21/6458 356/217 |
| 2011/0304723 A1* | 12/2011 | Betzig .................. G02B 21/002 348/79 |
| 2015/0226670 A1 | 8/2015 | Kleppe et al. |

OTHER PUBLICATIONS

F. C. Zanacchi et al.; "Live-cell 3D super-resolution imaging in thick biological samples"; Nature Methods, vol. 8, No. 12, doi:10.1038/nmeth.1744, Oct. 9, 2011 (14 pages).

J.C.M. Gebhardt et al.; "Single-molecule imaging of transaction factor binding to DNA in live mammalian cells" Nature Methods, doi:10.1038/nmeth.2411, Mar. 24, 2013 (9 pages).

International Search Report issued in PCT/EP2014/068139 dated Jan. 12, 2014 (2 pages).

Written Opinion of the International Searching Authority issued in PCT/EP2014/068139 dated Jan. 12, 2014 (7 pages).

\* cited by examiner

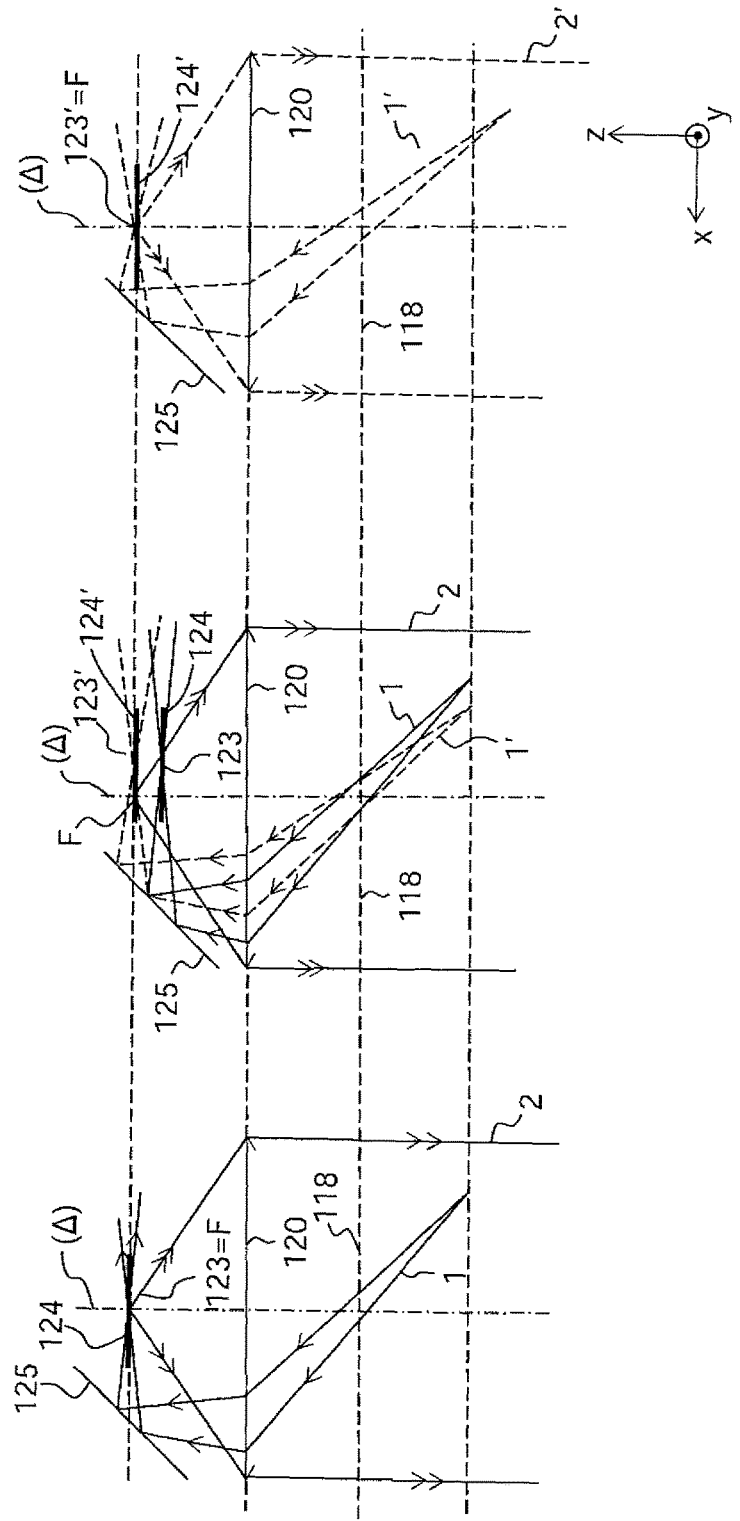

SYSTEM AND METHOD OF EDGE-ILLUMINATION MICROSCOPY

STATE OF THE ART

Technical Field of the Invention

The present invention relates to an edge-illumination microscopy system and method.

State of the Art

Optical microscopy makes it possible to track living cells in their native environment. Techniques that are for example known include florescence microscopy which allows for direct observation of the biological samples of small thickness or microscopy techniques which make it possible to produce images in thicker samples such as laser scanning confocal microscopy or multi-photon microscopy (nonlinear).

Recently, florescence microscopy devices for thick samples have been described, based on an edge-illumination of the sample, and known as light sheet-based illumination microscopes, or SPIM (for "Single-plane illumination microscopes"). SPIM microscopy consists in selectively illuminating a plane of the sample transversal to the axis of the microscope lens, making it possible to thus produce optical sections of the sample for deep imaging. Such devices are described for example in the US patent application 2011/0304723 implementing a Bessel beam illumination, in the article by R. Jorand et al. ("Deep and Clear Optical Imaging of Thick Inhomogeneous Samples" PlosOne Volume 7 Issue 4 (2012)), combining the SPIM technique with an adaptive optical loop on the detection pathway to enhance the quality of the image, in the article by F. Zanacchi et al. ("Live-cell 3D super resolution imaging in thick biological samples" Nature Methods/Vol. 8 No. 12 (2011)) applying the SPIM technique to super resolution microscopy, and also in the article by Gebhart et al. ("Single-molecule imaging of transcription factor binding to DNA in live mammalian cells" Nature Methods DOI:10.1038/NMETH 2411 (2013)) proposing an arrangement with two microscope lenses of parallel axes and a deflection mirror.

Hitherto, the SPIM technique has however always required the use of two microscope lenses placed at a distance close to the sample. In addition to the usual microscope lens on the detection pathway, making it possible to ensure the optical conjugation between the edge of the sample illuminated by the light sheet and the detection plane, a second microscope lens is necessary on the sample illumination pathway, to ensure the focusing of the light sheet in the sample, thus forming two independent illumination and detection pathways respectively. This constraint does however add significant mechanical complexity of implementation, does not allow for the use of standard microscopes and imposes limitations on the numerical aperture of the lenses used.

The invention proposes an edge-illumination microscopy system and method notably comprising an original control of the focusing of the light sheet, allowing for the use of a single microscope lens common to the illumination and detection pathways.

SUMMARY OF THE INVENTION

According to a first aspect, the invention relates to a microscopy system for a thick sample with edge-illumination of the sample, comprising a sample holder, a detection pathway and a sample illumination pathway.

The detection pathway comprises a microscope lens of given optical axis, a detection device comprising a detection surface optically conjugate with an object imaging surface in the object space of the microscope lens, and means for relative axial displacement of the microscope lens and of the sample holder.

The sample illumination pathway comprises at least one emission source of an illumination beam; means for forming, from the illumination beam, an illumination surface; said microscope lens; deflection means making it possible to deflect the illumination surface in the object space at the output of the microscope lens, to form a transverse illumination surface, situated in a plane substantially at right angles to the optical axis of the microscope lens; and illumination beam scanning means allowing a displacement of the transverse illumination surface along the optical axis of the microscope lens.

The microscopy system according to the first aspect further comprises focusing means making it possible to superimpose the object imaging surface and the transverse illumination surface, comprising means separate from the relative displacement means of the microscope lens and of the sample holder.

As will be detailed herein below, the object imaging "surface" and the transverse illumination "surface" are not strictly surfaces in the geometric sense of the word, but rather parallelepipedal volumes for which the aim is generally to render the thickness (dimension along the optical axis of the microscope lens) as thin as possible.

The "superposition" of the "object imaging surface" and of the "transverse illumination surface" thus consists in bringing into one and the same plane the median planes of the two parallelepipedal volumes and in centering them relative to one another laterally.

The architecture of the microscopy system thus produced makes it possible to control, in a system of SPIM type with a single microscope lens, the position of the transverse illumination surface or "light sheet" in the object space of the microscope lens, such that it remains superimposed on the object imaging surface of the lens, regardless of the relative position along the optical axis of the microscope lens between the microscope lens and the sample holder.

According to a variant, the focusing means comprise a wavefront spatial modulation device, situated in the detection pathway. The wavefront spatial modulation device can further allow, according to a variant, for the correction of at least a part of the optical defects between the sample and the detection surface.

The focusing means can also comprise means for varying the focusing of the illumination beam, making it possible to laterally center the transverse illumination surface on the object imaging surface. Such means are particularly advantageous in the case of significant displacements sought for the light sheet in the sample.

For example, the means for varying the focusing of the illumination beam can comprise an optical system with fixed power coupled to an optical system with variable focal length.

According to one example, the deflection means can be secured to the sample holder. That is particularly advantageous when the relative axial displacement means of the microscope lens and of the sample holder comprise axial displacement means for the sample holder. Thus, the displacement of the sample holder leads to the displacement of the deflection means.

According to a second aspect, the invention relates to an edge-illumination device adapted to a microscope comprising a microscope lens with an object imaging surface, means for relative axial displacement of a sample holder with the microscope lens and a detector with a detection surface optically conjugate with the object imaging surface.

The illumination device according to the second aspect comprises at least one emission source of an illumination beam and means for forming, from the illumination beam, an illumination surface. It further comprises a sample holder and deflection means secured to the sample holder, the deflection means being intended to deflect the illumination surface at the output of the microscope lens, to form a transverse illumination surface, situated in a plane substantially at right angles to the optical axis of the microscope lens. The illumination device according to the second aspect also comprises illumination beam scanning means allowing a displacement of the transverse illumination surface along the optical axis of the microscope lens and means for varying the focusing of the illumination beam, making it possible to laterally center the transverse illumination surface (124) on the object imaging surface.

Such a device makes it possible to easily convert a conventional wide-field fluorescence microscope into an edge-illumination microscopy system. The sample holder, provided with the deflection means, can be a part that can be disposed of after use, which replaces the usual microscope sample holder.

Advantageously, the incorporation of the edge-illumination device in the microscope can be done by means of a beam splitter or of a dichroic filter, which can already form part of the microscope, or which is supplied with the illumination device.

According to a third aspect, the invention relates to a microscopy method for a thick sample arranged on a sample holder, with edge-illumination of the sample, comprising:
- the emission of at least one illumination beam,
- the formation, from the illumination beam, of an illumination surface;
- the focusing of the illumination surface in the sample by means of a microscope lens of given optical axis and the deflection of the illumination surface deriving from the microscope lens allowing for the formation of a transverse illumination surface, situated in a plane substantially at right angles to the optical axis of the microscope lens;
- the formation, by means of said microscope lens, of the image of a zone of the sample illuminated by the transverse illumination surface on a detection surface of a detection device;
- the scanning of the illumination beam allowing a displacement of the transverse illumination surface along the optical axis of the microscope lens;
- the superposition, by focusing means comprising means separate from the relative axial displacement means of the microscope lens and of the sample, of the object imaging surface, conjugate in the object space of the microscope lens with the detection surface, and of the transverse illumination surface.

According to a variant, the superposition of the object imaging surface and of the transverse illumination surface can comprise a step of variation of the focusing of the illumination beam, allowing for a lateral centering of the transverse illumination surface on the object imaging surface.

According to a variant, the superposition of the object imaging surface and of the transverse illumination surface can comprise a step of spatial modulation of the wavefront emitted by the zone of the sample illuminated by the illumination surface, making it possible to bring the object imaging and illumination surfaces into one and the same plane.

According to a variant, the formation, from the illumination beam, of an illumination surface comprises the generation of a light pencil and the scanning of the light pencil.

BRIEF DESCRIPTION OF THE DRAWINGS

Other advantages and features of the invention will emerge on reading the description, illustrated by the following figures:

FIGS. 3A to 3C, diagrams illustrating, in three steps, the focusing of the illumination beam in the sample.

For consistency, the identical elements are identified by the same references in the different figures.

DETAILED DESCRIPTION

Figure 1A:
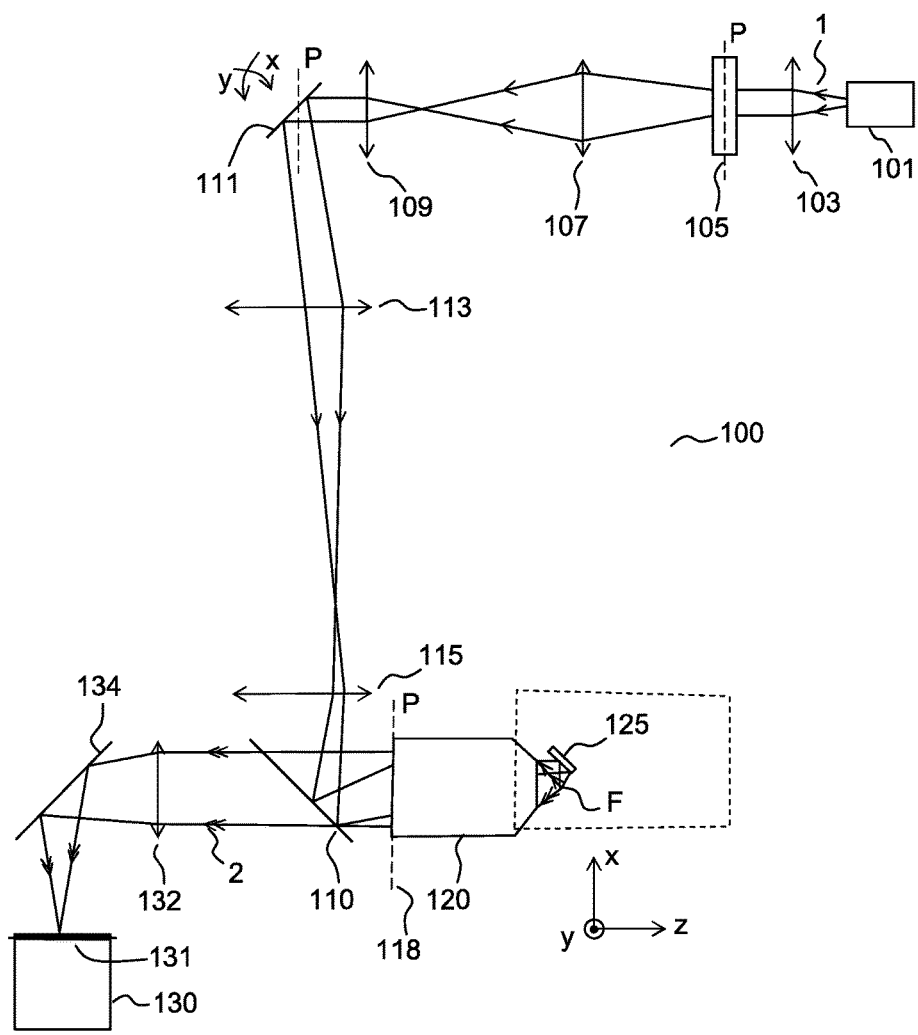
FIG. 1A, a diagram illustrating an edge-illumination microscope system, according to an exemplary embodiment of the invention.
Figure 1B:
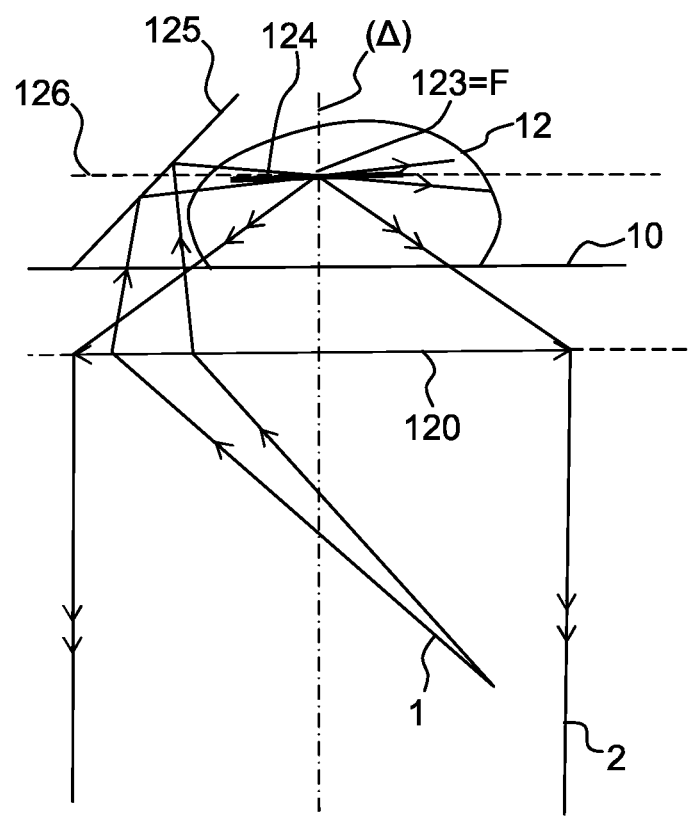
FIG. 1B, a diagram illustrating in more detail the focusing in a microscopy system of the type of FIG. 1A.

FIGS. 1A and 1B illustrate an edge-illumination microscopy system 100 according to an exemplary embodiment of the present description. FIG. 1B represents in more detail the part of the system outlined in dotted lines in FIG. 1A.

The microscopy system 100 comprises, in the example of FIGS. 1A and 1B, an illumination pathway and a detection pathway separated by a plate 110, for example a dichroic filter or a beam splitter, and comprising, in a common part, a microscopy lens 120.

The microscopy system further comprises sample holding means 12, comprising a plate 10 and relative displacement means for the sample holder and the microscope lens (not represented in the figures), making it possible to cover the zone of interest to be imaged. The holder displacement means comprise, for example, a motor-driven platform (not represented), for example a piezoelectric platform, making it possible to displace either the microscope lens, or the plate 10 intended to receive the sample 12, in a plane XY at right angles to the optical axis ($\Delta$) of the microscope lens and along the axis Z parallel to the optical axis ($\Delta$) of the microscope lens. The microscopy system is represented in the figures in the plane XZ, where XZ represents a reference frame of the object space of the microscope lens, that is to say a plane at right angles to the surface of the plate 10 of the sample 12, comprising the optical axis of the microscope lens.

The detection pathway is intended to form an image of a zone of interest of the sample on a detection surface 131 of detection means 130, for example comprising a matrix detector, for example an amplified camera of EMCCD type (EMCCD standing for "Electron Multiplying Charge Coupled Display"). The detection pathway comprises the microscope lens 120, intended to work, for example, in an infinity-focusing optical configuration, that is to say that, in the optimum working configuration, the beam 2 emitted by the sample at a point F of the center of the object field of the microscope lens (called "object imaging surface") is a beam collimated at infinity at the output of the microscope lens.

The detection pathway also comprises optical elements allowing for the formation of the image on the detection surface, for example an optic 132 and deflection means 134.

The illumination pathway comprises one or more emission sources 101 of a sample illumination beam 1, advantageously a spatially coherent light source, for example a fiber-drawn source in a single-mode fiber, for example a laser source. In one embodiment of the invention, a plurality of emission sources can be provided, for example to form illumination beams with different wavelengths, making it possible to excite different fluorophores in fluorescence applications, or respectively allowing for photo-activation, photo-conversion and excitation of fluorescent proteins in PALM applications for example. A lens 103 makes it possible to form a collimated beam from the source.

The sample illumination pathway further comprises means for forming, from the illumination beam, an illumination surface. These means can comprise very simply a lens with small numerical aperture (for example the lens 103) making it possible to form a light pencil of given diffraction length, associated with scanning means (obtained for example by a rotation of the rotary mirror 111) to form a surface. Alternatively, specific optics can be used to form the light pencil, for example non-diffractive optical elements, of axicon type, or elements adapted to form beams of Bessel beam type. Generally, the illumination surface will have a thickness directly linked to the diffraction length, as will be detailed hereinbelow. The means for forming the illumination surface can also comprise a cylindrical lens combined with the small aperture lens or the non-diffractive optical element, making it possible to dispense with the scanning means.

The illumination pathway further comprises the microscope lens 120 (represented in FIG. 1B by a convergent optic), the exit pupil of which is referenced 118. In FIG. 1A, the planes referenced P represent the conjugate planes of the planes of the exit pupil 118 of the microscope lens 120. The lenses 107, 109 on the one hand, and 113, 115 on the other hand, are relay optics ensuring the illumination beam transport and the conjugation of the pupil planes P.

In the object space of the microscope lens 120 there is the sample 12, and deflection means 125, the assembly formed by the microscope lens and the deflection means making it possible to image the illumination surface in a transverse illumination surface 124, situated in a plane 126 substantially at right angles to the optical axis of the microscope lens.

The dimensions of the transverse illumination surface and its thickness are defined by the parameters of the illumination pathway. For example, if the reference frame of FIG. 1B is taken, in the object space of the microscope lens, the dimension Y of the illumination surface is defined, for a given optical system of the illumination pathway, either by the amplitude of the scanning of the illumination beam in the direction Y, or by the amplitude of the astigmatism introduced by a cylindrical lens. The dimension X of the illumination surface and the thickness (along the axis Z) of the illumination surface are directly linked to the size of the excitation beam at the lens input and to the focal distance of the microscope lens. The expression "thickness of the illumination surface" should be understood to mean the size on the axis Z of the main lobe of the diffraction figure but also, in the case of Bessel-type illumination beams, the ratio between the light energy concentrated in this main lobe of the diffraction figure and the energy dispersed in the secondary lobes. Thus, if a thin transverse illumination surface is sought, typically of the same order of magnitude as the thickness of the object imaging surface, itself defined by the depth of field of the microscope lens, a transverse illumination surface will be obtained that is shorter on the X axis than if a significantly greater thickness of the illumination surface is accepted. Typically, for an ×100 microscope lens, of numerical aperture NA=1.3, the depth of field is less than 1 µm. The dimensions of the transverse illumination surface will typically be able to be between 10 and 50 µm on the X axis and approximately 100 µm on the Y axis. In all cases, a central point 123 of the transverse illumination surface 124 can be defined that corresponds to the point of best focus on X and to the geometrical center point on the Y axis. In the example of FIG. 1B, the central point 123 coincides with the object focus F of the microscope lens 120.

The deflection means comprise, for example, a micromirror inclined at 45° relative to the optical axis of the microscope lens. The deflection means must have a bulk compatible with microscope lenses of high numerical aperture. On the Y axis (see FIG. 1B), the size of the reflecting surface is advantageously substantially equivalent to the size of the field of the microscope lens used. On the axis inclined at 45°, the size of the useful reflecting surface can advantageously lie between a quarter and half of the field of the microscope lens. Because of this, the useful reflecting surface can be of the order of magnitude 50×200=10000 µm² for lenses of high enlargement (60× or 100×), 5 times greater for lenses of smaller enlargement (10× or 20×), the bulk around the reflecting surface having to be of the same order of magnitude as the reflecting surface. So as to be able to reflect the illumination beam deriving from the microscope lens, the useful surface of the deflection means must be situated in the useful field of the microscope lens.

Suitable deflection means can be formed by the holder (or "cantilever") of an atomic force microscopy point (see for example the article by Gebhart et al.), positioned at 45° from the optical axis of the microscope lens. They can also comprise a structured plate, for example of the type described in the published U.S. Pat. No. 7,974,003. According to a variant, the deflection means are designed to be secured to the sample holder, as will be explained below in the description.

The illumination pathway also comprises scanning means 111 for the illumination beam 1 allowing for a displacement of the transverse illumination surface 124 along the optical axis of the microscope lens.

Figure 2:
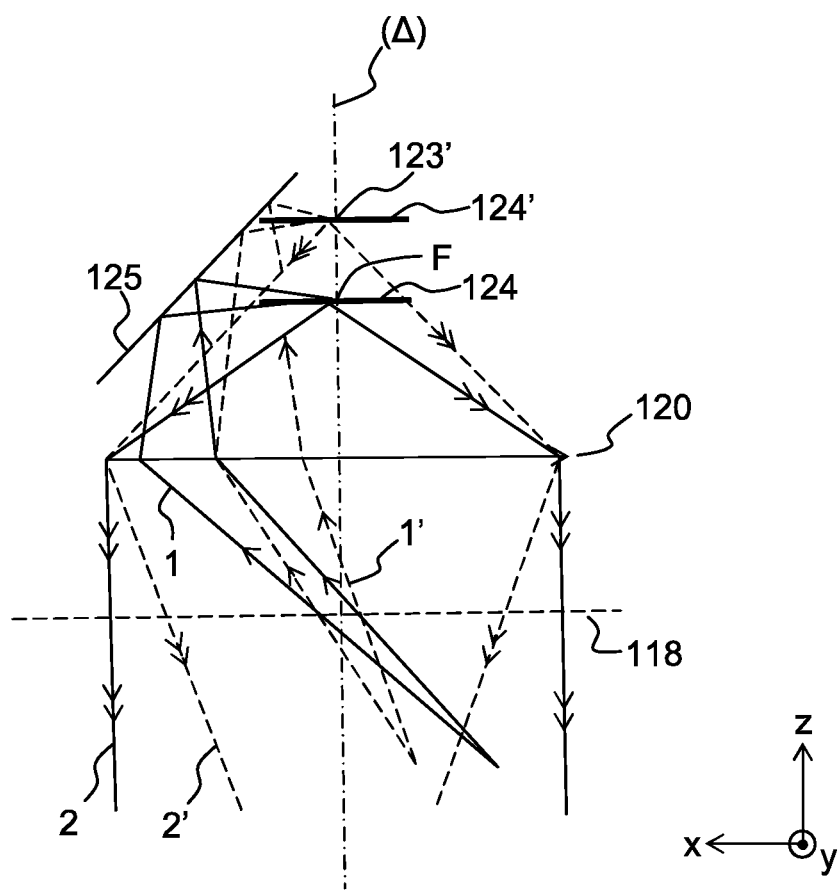
FIG. 2, a diagram illustrating the displacement of the light sheet along the axis Z in the object space of the microscope lens.

FIG. 2 illustrates the axial displacement of the transverse illumination surface in the microscopy system according to the present description.

As illustrated in FIG. 2, the displacement of the transverse illumination surface 124 along the optical axis Δ of the microscope lens (parallel to the axis Z) can be advantageously obtained by angular scanning of the incident illumination beam 1, leading to a lateral displacement of the beam (on the axis X in FIG. 2). This lateral displacement is reflected by an axial displacement of the illumination surface after reflection on the deflection means 125 of the incident beam, in the object space of the microscope lens. Advantageously, the axis of rotation of the angular scanning is situated in an optically conjugate plane of the pupil of the microscope. In the space of the microscope lens, the relationship which links the displacement ΔZ and the angular modification Δθ of the beam is as follows: $\Delta Z = f \times \Delta \theta$ in which f is the focal length of the microscope lens, this expression being valid in the context of small angles for which the tangent of an angle can be approximated to the angle itself. Since the angular field of microscope lenses is conventionally less than 10°, this approximation is valid for microscopy applications. Thus, in FIG. 2, the rotation of the beam 1 forms the beam 1', which results in a displacement ΔZ of the transverse illumination surface. This rotation can be obtained by the scanning means 111 of the illumination pathway, which comprise, for example, a rotary optic which makes it possible to produce the translation of the beam on the X axis to produce the axial displacement of the illumination surface and, optionally, on the Y axis to make the illumination surface by scanning of the illumination beam. This rotary optic can, for example, be a combination of galvanometric systems or a combination of MEMS mirrors (with one axis) or one MEMS mirror with two axes. In the case where two distinct mirrors are used to produce these two rotations, it is advantageous for the axes of rotation of these two mirrors to be optically conjugate.

It is thus possible, by virtue of the scanning means, to probe the sample by displacing the transverse illumination surface 124 along the optical axis of the microscope. By displacing the transverse illumination surface 124 as can be seen in FIG. 2, the zone of the sample that is illuminated is no longer located in the object working plane of the microscope lens, for example the object focal plane, and is no longer conjugate with the detection surface. The microscopy system according to the present description comprises focusing means, including means separate from the relative axial displacement means of the microscope lens and of the sample, which will make it possible to superimpose the transverse illumination surface and the object imaging surface (conjugate surface of the detection surface in the object plane of the microscope lens).

If the displacement is small, typically less than ten times the depth of field of the microscope lens, it is possible to correct the resultant defocusing on the detection pathway, simply by displacing the detection surface. The focusing means are reduced to axial displacement means for the detection surface. The focusing means can also comprise a wavefront spatial modulation device arranged on the detection pathway. The spatial modulation device can comprise a single optical lens (for example the lens 132) displaced to correct the focusing, or can comprise an optical system with variable power, a liquid crystal valve, a deformable mirror, etc. Focusing means on the detection pathway offer the advantage of adding no constraint nor any displacement of the microscope lens and/or the sample.

However, if the displacement is significant, the transverse illumination surface moves away from the object working plane for which the microscope lens has been designed, for example the object focal plane, and distancing significantly from this configuration can bring about not only significant optical aberrations but also a variation of the numerical aperture. The focusing means then advantageously comprise, in the illumination pathway, means 105 (see FIG. 1A) for varying the focusing of the illumination beam, making it possible to laterally center the transverse illumination surface 124 on the object imaging surface.

FIGS. 3A to 3C illustrate, according to one example, the adjustment of the focusing in the microscopy method according to the present description, implementing the means 105 for varying the focusing of the illumination beam.

FIG. 3A corresponds to FIG. 1B described previously, in which a beam 1 is focused in the form of a transverse illumination surface 124 in the object working plane of the microscope lens, for example the object focal plane. In this configuration, the beam 2 emitted by the sample (fluorescent light for example), is collimated at infinity at the output of the microscope lens, in the detection pathway, and perfectly focused on the detection surface of the detector. Thus, in the object space of the microscope lens, the transverse illumination surface and the object imaging surface, conjugate with the detection surface in the object space of the microscope lens, are superimposed.

FIG. 3B illustrates the case where the beam 1 is scanned (in the image space of the microscope lens) in order to displace the transverse illumination surface in the sample. The beam after scanning, referenced 1', makes it possible to form a transverse illumination surface 124' offset relative to the first position of the transverse illumination surface by a displacement Δz. To reposition the transverse detection surface 124' in the object working plane of the microscope, a relative displacement between the sample and the microscope lens on the optical axis of the microscope lens is performed. Thus, in FIG. 3B, the transverse illumination surface 124' is located at the same distance on the axis Z of the microscope lens as the transverse illumination surface 124 in FIG. 3A, that is to say in the object working plane of the microscope lens and the beam 2' emitted by the sample is once again collimated at infinity at the output of the microscope lens, in the detection pathway, then perfectly focused on the detection surface of the detector. However, the relative axial displacement of the sample and of the microscope lens induces, as appears in FIG. 3B, a lateral displacement of the transverse illumination surface. Thus, the best focus point 123, corresponding to the center of the transverse illumination surface, is offset relative to the optical axis of the microscope lens, this offset resulting from the relative axial displacement of the microscope lens and of the sample. In other words, the object imaging surface and the transverse illumination surface are indeed in the same plane, but off-center. The means 105 for varying the focusing of the illumination beam then make it possible to laterally recenter the transverse illumination surface 124 on the object imaging surface, as is illustrated in FIG. 3C.

The means 105 for varying the focusing comprise, for example, an optical lens with variable focal length (for example a lens of Varioptic®, Optotunes®, Polight® or LensVector® type) or a lens in which one or a group of lenses is mobile, or indeed a deformable mirror or else a liquid crystal valve.

Advantageously, the means 105 for varying the focusing are located in a plane optically conjugate with the pupil plane of the microscope lens which is, generally, positioned on the image focal plane of the microscope lens. In this way, the modification of the focusing plane of the illumination beam does not alter the beam size in the plane of the pupil of the microscope lens and, consequently, the thickness of the illumination surface.

In one embodiment of the invention, the means 105 for varying the focusing can be a combination of a system with fixed power coupled with a system with variable focal length. The system with fixed power can be used to compensate the mean focusing distance linked to the use of the deflection means (this distance is approximately equal to the radius of the field of view of the lens in the object space (space of the sample), i.e. 40 to 60 μm typically for a 100× lens). The means for varying the focusing are dimensioned to have an adjustable amplitude that is sufficient to cover the depthwise imaging range desired by the user. For example, if the depthwise field of excursion desired on the sample is 50 μm, it will be possible to choose means for varying the focusing that allow a displacement on Z of at least 50 μm around the mean focusing plane.

In one embodiment of the invention, the detection pathway can comprise a device for correcting optical aberrations introduced on the detection pathway (by the imaging optical system and by the sample itself). The device for correcting optical aberrations comprises, for example, a deformable mirror. It can be controlled by a device for analyzing optical defects, for example of Shack-Hartmann type. The device for correcting optical aberrations can also be used for the focusing adjustment, as was described previously. In the context of 3D microscopy of pointilliste type (PALM/STORM/SPT), the device for correcting aberrations can also be used to carry out the fashioning of the PSF so as to establish a bijective relationship between the shape of the PSF and the position on z of the emitting particle (as is described for example in the application FR2971693).

The microscopy system described thus makes it possible to make images in volume by producing images in a number of consecutive planes depthwise in the sample, by means of a single microscope lens.

It is also possible to adapt a known microscopy system for two-dimensional imaging, to produce a three-dimensional microscopy system, by virtue of an edge-illumination device according to the present description. A known microscope for two-dimensional imaging (wide field microscopy) typically comprises a microscope lens with an object imaging surface, relative axial displacement means for a sample holder with the microscope lens and a detector with a detection surface optically conjugate with the object imaging surface.

The edge-illumination device advantageously comprises at least one emission source for an illumination beam; means for forming, from the illumination beam, an illumination surface; a sample holder and deflection means secured to the sample holder, the deflection means being intended to deflect the illumination surface at the output of the microscope lens, to form a transverse illumination surface, situated in a plane substantially at right angles to the optical axis of the microscope lens; means for scanning the illumination beam allowing a displacement of the traverse illumination surface on the optical axis of the microscope lens; means for varying the focusing of the illumination beam, making it possible to laterally center the transverse illumination surface on the object imaging surface. All of these means have been described above in relation to the edge-illumination microscopy system.

According to a variant, the sample holder and the deflection means secured to the sample holder are supplied with the illumination device of the microscope to be adapted, by replacing the sample holder usually used.

The edge-illumination device and the microscopy system described in the present application can be applied to all the microscopy techniques that already benefit from the advantages of light sheet transverse-illumination technique, and notably to wide field fluorescence microscopy and to super-resolution microscopy of pointilliste type (PALM/STORM/SPT). In these two types of microscopy, the light sheet transverse illumination makes it possible to obtain an optical "sectioning" effect (only the edge of interest is illuminated), and makes it possible to obtain a better signal-to-noise ratio of the detection signal because only the edge imaged is illuminated; there is therefore no stray light originating from the layers of the sample situated on either side of the imaged plane, making it possible to image individual molecules at greater depth. The microscopy system applies also to non-linear microscopy, or else structured illumination microscopy SIM.

Although described through a certain number of exemplary embodiments, the microscopy method according to the invention and the device for implementing said method comprise different variants, modifications and refinements which will become obviously apparent to a person skilled in the art, given that these different variants, modifications and refinements form part of the scope of the invention as defined by the following claims.

The invention claimed is:

1. A microscopy system for a thick sample with edge-illumination of the sample, comprising:
   a sample holder;
   a detection pathway comprising:
     a microscope lens of given optical axis and exit pupil;
     a detection device comprising a detection surface optically conjugate with an object imaging surface in the object space of the microscope lens;
     means for relative axial displacement of the microscope lens and of the sample holder;
   a sample illumination pathway comprising:
     at least one emission source of an illumination beam;
     means for forming, from the illumination beam, an illumination surface;
     said microscope lens;
     deflection means making it possible to deflect the illumination surface in the object space at the output of the microscope lens, to form a transverse illumination surface, situated in a plane substantially at right angles to the optical axis of the microscope lens;
     scanning means for an angular scanning of the illumination beam, allowing a displacement of the transverse illumination surface along the optical axis of the microscope lens;
   the microscopy system further comprising:
     optical means for varying the focusing of the illumination beam, making it possible to laterally center the transverse illumination surface on the object imaging surface, wherein said optical means are separate from the relative axial displacement means; and
     relay optics configured for optically conjugating a plane of a pupil of said optical means for varying the focusing of the illumination beam with a plane of the exit pupil of the microscope lens.

2. The microscopy system as claimed in claim 1, in which the optical means for varying the focusing of the illumination beam comprise an optical system with fixed power coupled to an optical system with variable focal length.

3. The microscopy system as claimed in claim 1, further comprising a wavefront spatial modulation device, situated in the detection pathway, in which the wavefront spatial modulation device allows for the correction of at least a part of the optical defects between the sample and the detection surface.

4. The microscopy system as claimed in claim 1, in which the deflection means are secured to the sample holder.

5. The microscopy system as claimed in claim 1, in which the means for forming the illumination surface comprise means for generating a light pencil and means for scanning the light pencil.

6. The microscopy system as claimed in claim 1, in which the means for forming the illumination surface comprise a cylindrical lens.

7. The microscopy system as claimed in claim 1, in which said pupil of the optical means for varying the focusing of the illumination beam is located in a plane optically conjugated with a plane comprising an axis of rotation of said scanning means.

8. An edge-illumination device adapted to a microscope comprising a microscope lens with an object imaging surface, means for relative axial displacement of a sample holder with the microscope lens and a detector with a detection surface optically conjugate with the object imaging surface, the illumination device comprising:
- at least one emission source of an illumination beam;
- means for forming, from the illumination beam, an illumination surface;
- a sample holder and deflection means secured to the sample holder, the deflection means being intended to deflect the illumination surface at the output of the microscope lens, to form a transverse illumination surface, situated in a plane substantially at right angles to the optical axis of the microscope lens;
- illumination beam scanning means allowing a displacement of the transverse illumination surface along the optical axis of the microscope lens;
- optical means for varying the focusing of the illumination beam, making it possible to laterally center the transverse illumination surface on the object imaging surface, wherein said optical means are separate from the relative axial displacement means; and
- relay optics configured for optically conjugating a plane of a pupil of said optical means for varying the focusing of the illumination beam with a plane of the exit pupil of the microscope lens.

9. A microscopy method for a thick sample arranged on a sample holder, with edge-illumination of the sample, comprising:
- the emission of at least one illumination beam;
- the formation, from the illumination beam, of an illumination surface;
- the focusing of the illumination surface in the sample by means of a microscope lens of given optical axis and exit pupil and the deflection of the illumination surface deriving from the microscope lens allowing the formation of a transverse illumination surface, situated in a plane substantially at right angles to the optical axis of the microscope lens;
- the formation, by means of said microscope lens, of the image of a zone of the sample illuminated by the transverse illumination surface on a detection surface of a detection device;
- the scanning of the illumination beam allowing a displacement of the transverse illumination surface along the optical axis of the microscope lens;
- the variation of the focusing of the illumination beam, allowing for a lateral centering of the transverse illumination surface on the object imaging surface, conjugate in the object space of the microscope lens with the detection surface, by optical means separate from the relative axial displacement means; and
- the optical conjugation, by relay optics, of a plane of a pupil of said optical means for varying the focusing of the illumination beam with a plane of the exit pupil of the microscope lens.

10. The microscopy method as claimed in claim 9, further comprising the correction of at least a part of the optical defects between the sample and the detection surface using a wavefront spatial modulation device.

11. The microscopy method as claimed in claim 9, in which the formation, from the illumination beam, of an illumination surface comprises the generation of a light pencil and the scanning of the light pencil.

* * * * *